United States Patent
Ritter et al.

(10) Patent No.: US 9,414,892 B2
(45) Date of Patent: Aug. 16, 2016

(54) DEVICE FOR CONTROLLING MARKER WIRE

(71) Applicant: Cook Medical Technologies LLC, Bloomington, IN (US)

(72) Inventors: Grant S. Ritter, Bloomington, IN (US); Thomas W. McGhie, Bloomington, IN (US); Thomas A. Osborne, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 576 days.

(21) Appl. No.: 13/802,979

(22) Filed: Mar. 14, 2013

(65) Prior Publication Data
US 2013/0289359 A1   Oct. 31, 2013

Related U.S. Application Data

(60) Provisional application No. 61/640,232, filed on Apr. 30, 2012.

(51) Int. Cl.
*A61B 19/00* (2006.01)
*A61B 17/00* (2006.01)

(52) U.S. Cl.
CPC .............. *A61B 19/54* (2013.01); *A61B 90/39* (2016.02); *A61B 2017/00951* (2013.01); *A61B 2090/3908* (2016.02); *A61B 2090/3987* (2016.02); *A61B 2090/3991* (2016.02)

(58) Field of Classification Search
CPC ............... A61B 19/54; A61B 2017/00951; A61B 2019/5487; A61B 2019/5491; A61B 2019/5408
See application file for complete search history.

(56) References Cited

U.S. PATENT DOCUMENTS

| 4,592,356 | A | 6/1986 | Gutierrez |
| 5,221,269 | A | 6/1993 | Miller et al. |
| 5,409,004 | A | 4/1995 | Sloan |
| 6,544,269 | B2 | 4/2003 | Osborne et al. |
| 2010/0022962 | A1 | 1/2010 | Bierman et al. |
| 2010/0256487 | A1* | 10/2010 | Hawkins ........... A61M 25/0028 600/434 |

FOREIGN PATENT DOCUMENTS

| EP | 1 769 770 A1 | 4/2007 |
| GB | 2 484 719 | 4/2012 |
| WO | WO 2007/059276 A1 | 5/2007 |

* cited by examiner

*Primary Examiner* — Gregory Anderson
*Assistant Examiner* — Son Dang
(74) *Attorney, Agent, or Firm* — Woodard, Emhardt, Moriarty, McNett & Henry LLP

(57) ABSTRACT

Arrangements are disclosed in which proximal portions of a marker wire are effectively secured. In one embodiment, a proximal portion of the marker wire is positioned inside a tubular member that allows for slidable movement of the marker wire within the tubular member. In some embodiments, a proximal portion of the marker wire is coupled to a spring member. Some embodiments also disclose a movement-resisting member having flaps that contact the surface of the marker wire and resist movement of the marker wire in one or more directions.

16 Claims, 8 Drawing Sheets

DEVICE FOR CONTROLLING MARKER WIRE

CROSS-REFERENCE TO RELATED APPLICATIONS

This application claims the benefit of U.S. Provisional Application No. 61/640,232, filed Apr. 30, 2012, which is hereby incorporated by reference in its entirety.

BACKGROUND

The present disclosure relates generally to medical devices and in particular aspects to apparatuses and methods for controlling an implanted marker wire.

It has become almost axiomatic that earlier detection of malignancies lead to improved patient survival rates. Improved mammographic techniques, for example, result in the earlier detection of smaller lesions in the breast. Accurate preoperative localization of lesions (that is, the determination of their size and position) serve two important concerns simultaneously: the successful extraction of a suspect lesion, without the removal of unduly large amounts of normal breast tissue. It may of course be desirable to locate cancerous or other tumors, foreign bodies, normal tissue structures or other objects within the body or within an organ of the body. Such locations include the liver, ductal structures, brain, lungs or other portions of a human or veterinary patient.

The localization of lesions which cannot be palpated is of particular concern, precisely since they cannot be palpated by the surgeon during surgery. Lesions may be nonpalpable because they are small in size and therefore difficult to locate (especially in large breasts), or because they are located deep within the tissue mass of the breast. Currently, such lesions are often initially located by radiology or ultrasound, and the lesion marked by a localization needle assembly prior to biopsy or surgery. Such needle assemblies have included a hypodermic needle or cannula which is inserted in the body to an area adjacent to and in contact with the lesion of interest. A marking wire (commonly referred to as a "hookwire" or "hookwire-type" stylet) is then inserted through the needle or cannula into the lesion and anchored in place. The needle or cannula is then removed, leaving the distal portion of the marking wire in place inside of the body and the proximal portion of the marker wire outside of the body Currently, the proximal portion of the marker wire is taped to the patient's skin to help maintain the marker wire's positioning inside of the patient's body and keep the protruding portion of the marker wire out of the patient's way. Unfortunately, one effect of taping the exposed portion of the marker wire to the skin is to over-constrain the wire when the skin moves relative to the lesion, for example when twisting or extending an arm. This may cause discomfort to the patient, cause the wire to come unsecured from the patient's skin, and/or cause the distal end of the wire marking the lesion to migrate from the target location. Thus there is a need for alternative securing arrangements that effectively secure the exposed portion of the marker wire.

SUMMARY

The present disclosure provides, in certain aspects, unique devices and methods for controlling one or more marker wires for use in localization procedures, particularly breast lesion localization procedures. In accordance with some forms of the disclosure, such devices and methods are arranged to slidably couple a proximal portion of a marker wire to the body of the patient.

In some aspects, a method for securing a localization marker wire includes providing access through a penetration site to a desired location in a patient; advancing a marker wire through the access to the desired location such that a distal end region of a marker wire secures in the desired location and the marker wire extends from the desired location proximally through the skin of the patient to a proximal end region having a proximal wire portion; and inserting the proximal wire portion of the marker wire into a wire retaining member arranged to slidably couple the proximal wire portion to the skin of the patient.

In further aspects, the method may include securing the wire-retaining member to the skin of the patient. And in some aspects the step of securing the wire-retaining member to the skin of the patient includes using an adhesive member. In some embodiments, the method may include a wire-retaining member encapsulating the marker wire and/or wherein the wire-retaining member includes a movement-resisting member arranged to resist movement of the proximal wire portion with respect to the wire-retaining member.

Portions of the present disclosure describe a kit having a packaging member retaining: a marker wire having a distal end region arranged for securement in a desired location inside a patient and a proximal end region having a proximal wire portion; a wire-retaining member arranged to be secured to the patient and receive the proximal wire portion; wherein the wire-retaining member slidably couples said proximal wire portion of the marker wire to the patient. In some aspects, the wire-retaining member confines movement of the marker wire to a direction substantially along the length of the proximal wire portion. The kit may include an adhesive member on the wire-retaining member arranged to couple the wire-retaining member to the body of a patient. In some embodiments, the wire-retaining member of the kit comprises a tube defining an internal lumen arranged to receive the proximal wire portion and/or the wire-retaining member comprises a movement-resisting member arranged to resist the marker wire from movement in a direction substantially along the length of the proximal wire portion, with respect to the wire-retaining member.

In some aspects, a marker wire-retaining device includes a wire-retaining member arranged to be secured to the patient and defining a wire-receiving region arranged to receive a proximal wire portion of a marker wire; and an adhesive member arranged to couple the wire-retaining member to the body of a patient; wherein the wire-retaining member slidably couples the proximal wire portion to the patient. In some embodiments the wire-receiving region may define a path having a curved portion and/or the device may further comprise a movement-resisting member coupled to the wire-retaining member and arranged to contact the proximal portion of the marker wire and resist movement of the marker wire in a direction along the length of the proximal wire portion.

While particular features and/or variations of particular features are disclosed herein with reference to particular embodiments, it should be appreciated that it is not intended for those features and/or variations of features to be limited to such. For example, embodiments of the present disclosure may comprise a wire-retaining member having a sidewall that defines apertures extending from and/or between and exterior surface and an interior surface of the sidewall and/or arranged to receive a proximal portion of a marker wire. As will be appreciated by those of ordinary skill in the art, other embodiments, although not illustrated with this feature, may also incorporate this feature and/or others.

Similarly, the present disclosure intends that numerous embodiments may comprise an inner lumen arranged to receive a proximal portion of a wire, such as a marker wire. For example, the surface defining the inner lumen may be arranged so as to achieve a desired frictional resistance between the wire and the wire-retaining device. Embodiments may also be arranged so that portions of the wire-retaining member encapsulate or partially surround a portion of the wire.

Various embodiments may be arranged so that the wire-retaining member confines movement of the wire to one or more directions. For example, the wire-retaining member may be arranged to confine movement of a marker wire to a direction that lies substantially along the length of the proximal wire portion, such to a direction lying along the longitudinal axis of the contained wire portion.

Several embodiments of the present disclosure may also comprise a movement-resisting member that resists movement of the wire retained by a portion of the wire-retaining member along one or more directions. For example, a spring member and/or a mechanical damper may be attached to a proximal portion of a marker wire so as to resist movement of the marker wire with respect to the wire-retaining member. In some instances, the movement-resisting member applies a predetermined force and/or a variable force to the marker wire. Additionally or alternatively, the force applied to the wire may vary depending on the movement of the wire, such as the distance of travel and/or the speed or acceleration of the marker wire with respect to the wire-retaining member. Several embodiments may also bias movement of a wire in one direction or another, such as by providing a greater resistance to movement in one or more directions than other directions. A movement-resisting member may also be arranged to limit the distance and/or the direction that a wire may travel.

While discussed with reference to perhaps one embodiment, a number of embodiments may comprise a guiding member arranged for positioning on a proximal portion, such as a proximal end, of a wire retained by the wire-retaining member. Such a guiding member may be arranged to guide movement of the wire with respect to the wire-retaining member.

As will be appreciated by those of ordinary skill in the art, the wire-retaining members of the present disclosure may have a variety of shapes and dimensions. For example, the wire-retaining member may have any of a variety of closed and/or open cross-sectional shapes, including but not limited to circular cross-sections and polygonal cross-sections, just to name a few non-limiting examples. Additionally, elongate wire retaining members may have curved sections, straight sections, and/or a mixture of the two. In some instances, the wire-retaining member can have overlapping portions and/or recessed portions arranged to receive another portion of the wire-retaining member.

Preferably, the wire-receiving region of the wire-retaining member is arranged to receive a wire. For example, the inner lumen of a wire-retaining member can have portions arranged to be the same size, substantially the same size, smaller than, and/or larger than the outer cross-sectional dimension of the wire. As a more particular example, for a marker wire having a maximum cross-sectional dimension (e.g., a diameter) of 0.5 millimeters, the dimension of the wire-receiving region (e.g., the inner lumen) may be 0.5 millimeters, substantially 0.5 millimeters, less than about 0.5 millimeters, or more than about 0.5 millimeters. In some instances, the wire-receiving region of the wire-retaining member defines a void and/or cavity having a dimension of at least 1 mm. More preferably, in some embodiments, the void and/or cavity has a dimension of 1 mm to 5 mm.

Preferably, the wire-retaining member is arranged to receive the wire so that at least the proximal end of the wire is retained within the wire-retaining member. For example, in some instances, a portion of the wire-retaining member, such as the wire-receiving region, has a length sufficient to receive the length of wire extending from the body of the patient. As a more particular example, if a 5 cm length of marker wire extends out of the skin of the patient, it is may be preferable that the wire-receiving region of the wire-retaining member have a length of at least 5 cm so that it may fully retain, conceal, and/or protect the portion of the marker wire extending out of the skin of the patient. In some instances, the wire-receiving region has a length of at least 5 cm. More preferably, the wire receiving region additionally or alternatively has a length of less than 30 cm.

Embodiments of the wire-retaining member disclosed herein may comprise a base and/or an adhesive arranged to provide structural support to the wire-retaining member and/or to adhere the wire-retaining member to the patient. In some instances, the base member and/or adhesive are arranged so that the wire-retaining member may conform to the surface contours of the patient's skin. As will be appreciated by one of ordinary skill in the art in view of this disclosure, the base member and/or adhesive may be positioned between the wire-retaining member and the skin of the patient when the device is attached to a patient's skin, or the base member and/or adhesive may extend beyond and/or between portions of the wire-retaining member. For instance, in some instances the base member and/or adhesive comprise portions for displaying information about the patient, the wire, and/or the wire-retaining member. Alternatively or additionally, the base member, adhesive, and/or wire-retaining member may be colored to aid in the concealment and/or visual appearance of the device. The base member and/or adhesive may also defined one or more openings for receiving a wire extending from the patient's skin.

Preferably, the wire-retaining member is arranged so as to have a low-profile (i.e., a low height above the surface of the patient's skin). For example, in some preferred embodiments the wire-retaining member, when attached to the skin of a patient and retaining a wire, extends less than 1 cm above the surface of the skin of the patient. More preferably, the wire-retaining member extends a distance of 5 mm or less above the surface of the patient's skin.

Devices incorporating some or all of the features and/or variations of features disclosed herein may be included in a kit individually or in combination with other devices useful for the positioning and/or securing of an external wire portion. Advantageously, these kits may be sterily sealed and packaged to aid. Preferably, marker wires will be provided with corresponding wire-retaining members arranged to receive and retain a portion of the wire for at least the period of time between the emplacement of the distal wire portion within the body of the patient and the surgical procedure to access the target site marked by the distal wire portion.

Other objects, embodiments, forms, features, advantages, aspects, and benefits of the present disclosure shall become apparent from the detailed description and drawings included herein.

DETAILED DESCRIPTION

Figure 1:
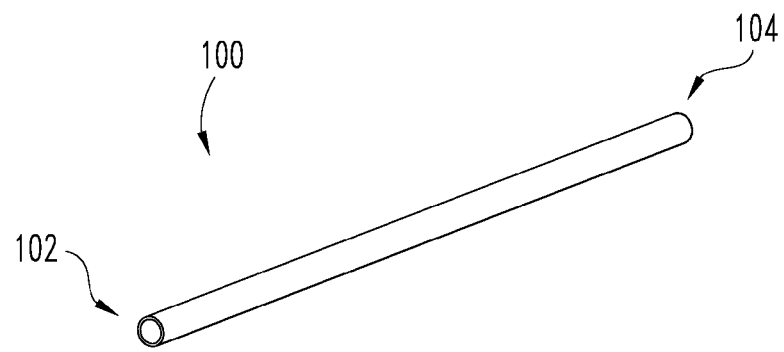
FIG. 1 is a perspective view of one embodiment of a wire-retaining member.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

With respect to the specification and claims, it should be noted that the singular forms "a", "an", "the", and the like include plural referents unless expressly discussed otherwise. As an illustration, references to "a device" or "the device" include one or more of such devices and equivalents thereof. It also should be noted that directional terms, such as "up", "down", "top", "bottom", and the like, are used herein solely for the convenience of the reader in order to aid in the reader's understanding of the illustrated embodiments, and it is not the intent that the use of these directional terms in any manner limit the described, illustrated, and/or claimed features to a specific direction and/or orientation.

The reference numerals in the following description have been organized to aid the reader in quickly identifying the drawings where various components are first shown. In particular, the drawing in which an element first appears is typically indicated by the left-most digit(s) in the corresponding reference number. For example, an element identified by a "100" series reference numeral will likely first appear in FIG. 1, an element identified by a "200" series reference numeral will likely first appear in FIG. 2, and so on.

Lesions within the body of a patient are often initially located by radiology or ultrasound, and the lesion marked by a localization needle assembly prior to biopsy or surgery. Such needle assemblies may include a hypodermic needle or cannula which is inserted in the body to an area adjacent to and/or in contact with the lesion of interest. A marking wire (commonly referred to as a "hookwire" or "hookwire-type" stylet) is then inserted through the needle or cannula into a position in or near the lesion and anchored in place. The needle or cannula is then removed, leaving the distal portion of the marking wire in place inside of the body and the proximal portion of the marker wire outside of the body. It is preferable that the proximal portion of the marker wire be secured so as to prevent migration of the distal portion of the marker wire and/or to reduce the discomfort and obtrusiveness the marker wire causes to the patient. Exemplary arrangements for securing the proximal portion of the marker wire are disclosed herein.

While the following embodiments are discussed with reference to a localization marker wire useful to mark a lesion within a breast of a patient, it should be appreciated that the present disclosure is not intended to be limited to such. As will be appreciated by those of ordinary skill in the art, the present disclosure may be used and/or arranged to secure a portion of a wire that extends into any number of locations within the body of a patient, including but not limited to breast tissue. Similarly, while portions of the present disclosure describe securing a proximal portion of a breast lesion localization marker wire, it should be appreciated that the present invention may also be used and/or arranged to secure a portion of a variety of wires, such as a wire guides.

Figure 2:
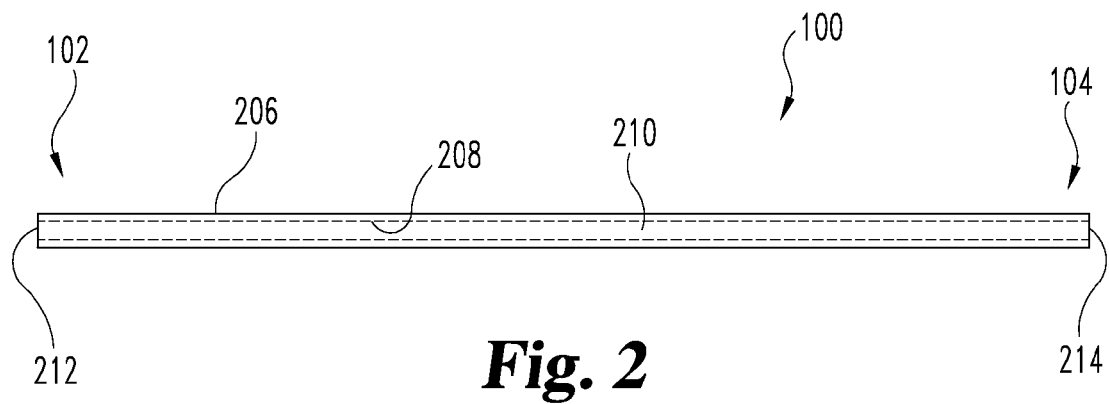
FIG. 2 is an elevational side view of one embodiment of a wire-retaining member.

FIG. 1 illustrates a perspective view of an elongate wire-retaining member 100 having a distal portion 102 and a proximal portion 104 near opposing ends of the wire-retaining member 100. As shown in FIG. 2, the wire-retaining member 100 may be in the shape of a hollow tube and have an exterior surface 206 and an interior surface 208 that defines an inner lumen 210. In some embodiments the inner lumen 210 extends from a distal opening 212 in the distal portion 102 of the wire-retaining member 100 to a proximal opening 214 in the proximal portion 104.

In some embodiments the inner lumen 210 extends from one end of the wire-retaining member 100 in the distal portion 102 to another end of the wire-retaining member 100 in the proximal portion 104. In other embodiments, the inner lumen 210 extends only a portion of the distance between two ends of the wire-retaining member 100. For example, the inner lumen may extend from a distal opening 212 towards the proximal portion 104 and terminate in a closed end prior to reaching an end of the wire-retaining member 100. The sidewall of the wire-retaining member 100 may also define apertures that extend from the exterior surface 206 to the interior surface 208, so as to allow a wire to access the inner lumen 210 at a point between the ends of the wire-retaining member 100.

In some instances, the inner lumen 210 is arranged to receive a proximal portion of a marker wire. The inner surface 208 defining the inner lumen 210 of the wire-retaining member 100 may be arranged to slidably couple the proximal portion of the marker wire to the wire-retaining member 100. In some instances, a smooth inner surface 208 is desired so as to allow the proximal portion of the marker wire to move in relation to the wire-retaining member 100 with little resistance. In other instances, a textured and/or roughened inner surface 208 may be desired so as to provide a resistance to movement of the proximal portion of the marker wire inside of the inner lumen 210.

In some embodiments, the wire-retaining member 100 may encapsulate the proximal portion of the marker wire. For example, the marker wire may be slidably inserted into the inner lumen 210 with the wall portion of the wire-retaining member 100 encircling the marker wire. Alternatively or additionally, portions of the wire-retaining member 100 may partially surround a portion of the marker wire. For example the wire-retaining member 100 may form a channel, such as a U-channel, with a side of the channel being unconstrained by a wall of the wire-retaining member 100. Such an arrangement may not constrain a marker wire positioned within the channel on all sides. The wire-retaining member, however, may still sufficiently control the proximal portion of the marker wire. For example, the wire-retaining member 100 may couple the marker wire in a slidable relationship to the skin of the patient. Additionally, the wire-retaining member 100 may protect the proximal portion of the marker wire from contact with the clothing of the patient.

Should a medical professional desire, an open-wall portion of the channel-type wire-retaining member 100 (e.g., the side of the channel being unconstrained by a wall of the wire-retaining member 100) may be placed against the skin of the patient and/or sealed with an additional member, such as a piece of tape. In this type of arrangement, for example the skin and/or tape closing a portion of the wire-retaining member, the combination of the wall of the wire-retaining member and the skin and/or additional member may encapsulate a proximal portion of the marker wire positioned within the channel.

In some embodiments, the wire-retaining member 100 confines movement of the marker wire to a direction substantially along the length of the proximal wire portion. For example, the wire-retaining member 100 may define an inner lumen 210 that is substantially the size of the marker wire and/or slightly larger than the received portion of the marker wire. When a portion of the marker wire is positioned inside of the inner lumen 210, the received marker wire portion is confined to movement substantially along the longitudinal axis of that marker wire portion.

Figure 3:
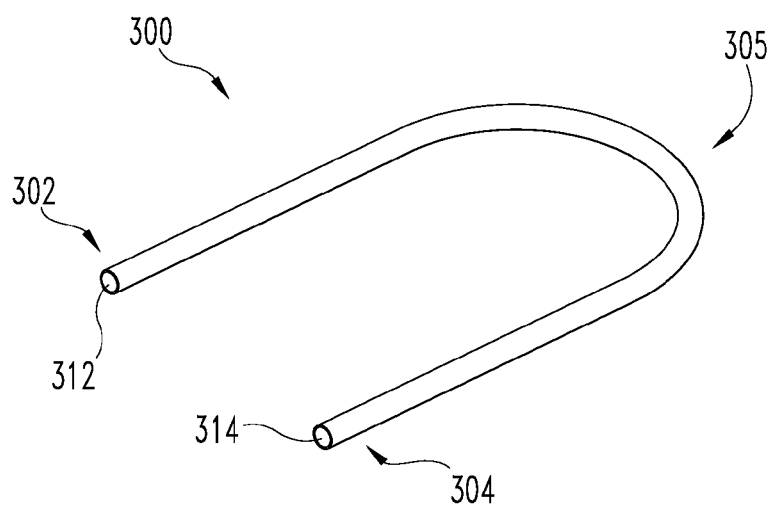
FIG. 3 is a perspective view of one embodiment of a wire-retaining member.

FIG. 3 illustrates one embodiment of a wire-retaining member 300 having a distal portion 302 and a proximal portion 304 separated by curved portion 305 such that the proximal portion 304 bends back towards the distal portion 302 of the wire-retaining member 300 and/or a penetration site, where the marker wire enters the body of the patient. The wire-retaining member has a wire receiving region, such as an inner lumen, that is arranged to receive a proximal portion of a marker wire. In some instances, the distal portion 302 has a distal opening 312 that communicates with the inner lumen. The inner lumen also may communicate with a proximal opening 314. In some embodiments, the wire-retaining member 300 and/or the inner lumen define a curved path for the proximal portion of the marker wire.

Embodiments of the wire-retaining member 300 having curved sections, such as curved portion 305, can reduce the discomfort of wearing a wire-retaining member and/or a marker wire. Having a curved section contact the skin is more comfortable than having an edge, end, and/or sharp bend such as a corner poking into the skin of a patient. Additionally, curved sections can offer a compact wire-retaining member 300 capable of retaining a significant length of marker wire in a compact area with little obtrusiveness to the patient. A curved section allows for an arrangement of a wire-retaining member 300 that occupies a small area on the skin of a patient, and therefore is less cumbersome to wear and obtrusive to movement of the patient. In some instances, the wire-retaining member 300 can be arranged so as to extend only a slight distance away from the surface of the skin, sometimes referred to as a "low profile".

Similar to the variations discussed with regard to wire-retaining member 100 disclosed above, the inner lumen may extend only a portion of the distance from one end of the wire-retaining member 300 to another end. Additionally, the inner surface defining the inner lumen of the wire-retaining member 300 may be smooth or have a texturing and/or roughening to control the movement of a proximal portion of a marker wire positioned within the inner lumen of the wire-retaining member 300.

Figure 4:
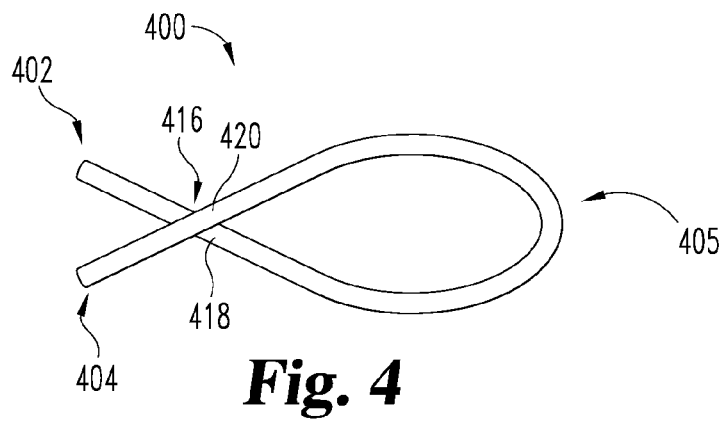
FIG. 4 is a plan view of one embodiment of a wire-retaining member.
Figure 5:
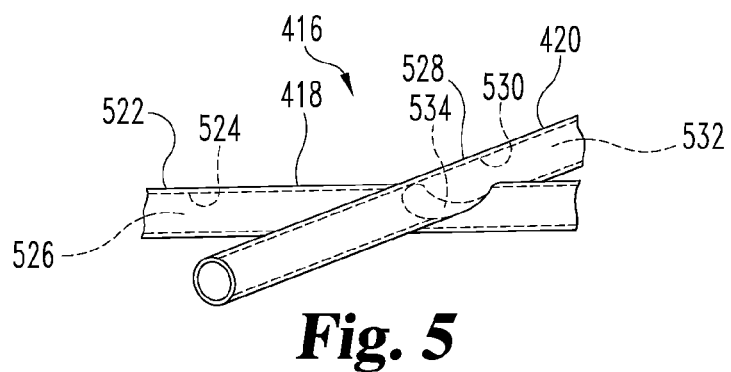
FIG. 5 is a perspective view of a portion of the wire-retaining member shown in FIG. 4.

FIGS. 4 and 5 illustrate an embodiment of a wire-retaining member 400 comprising a distal portion 402, a curved portion 405, and a proximal portion 404. As illustrated, the wire-retaining member 400 can cross itself and/or have an overlapping portion in a coincident region 416 in which a first portion 418 and a second portion 420 cross and/or overlap one another. In some embodiments, the wire-retaining member may be arranged to resemble a ribbon-shape.

In some embodiments, the first portion 418 and/or the second portion 420 has/have one or more recessed portions arranged to receive the other first or second portion 418, 420. For example, the first portion 418 may have a groove arranged to receive the second portion 420. This type of arrangement decreases the height of the device, i.e., the distance that the second portion 420 extends above the surface of the skin of the patient and/or out of the plane of the first portion 418. In some instances, it is preferred that the first portion 418 and the second portion 420 occur substantially in the same plane so as to form a low-profile wire-retaining member 400. A low profile wire-retaining member 400 may be preferable so as to reduce the visibility of the wire-retaining member 400 positioned under the clothing of the patient and/or to reduce the obtrusiveness of the wire-retaining member 400 to the activities of the patient.

In some embodiments, an inner lumen of the first portion 418 and an inner lumen of the second portion 420 may communicate with one another in the coincident region 416. FIG. 5 illustrates the coincident region 416 in closer detail where the first portion 418 and the second portion 420 cross one another. The first portion 418 has an outer surface 522 and an inner surface 524 defining a first inner lumen 526. The second portion 420 has an outer surface 528 and an inner surface 530 that defines a second inner lumen 532. The first and second inner lumens 526 and 532 communicate with one another in an intersecting region 534.

In some instances, the first inner lumen 526 and the second inner lumen 532 are different portions of one lumen extending through the wire-retaining member 400. For example, the first lumen may start in the distal portion 402 and extend into and through the curved portion 405 meeting the second inner lumen 532 that terminates in the proximal portion 404 of the wire-retaining member 400. This type of arrangement may permit a proximal portion of a marker wire to be positioned inside of the first inner lumen 526 and extend from the distal portion 402 of the wire-retaining member 400 through the curved portion 405 towards the proximal portion 404, passing the coincident region 416 and terminating in the second inner lumen 532. Alternatively, the proximal portion of a marker wire may extend from the distal portion 402 to the coincident region 416 and then into the proximal portion 404, bypassing the curved portion 405.

Figure 6:
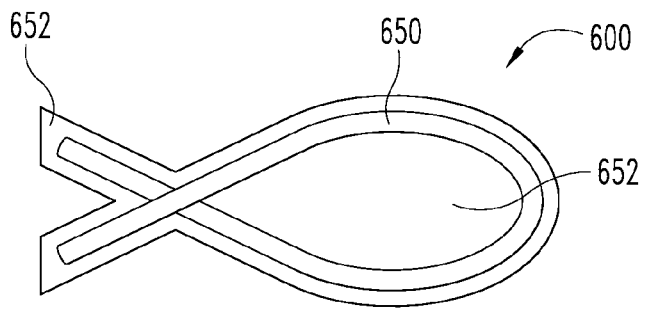
FIG. 6 is a plan view of one embodiment of a wire-retaining member.
Figure 7:
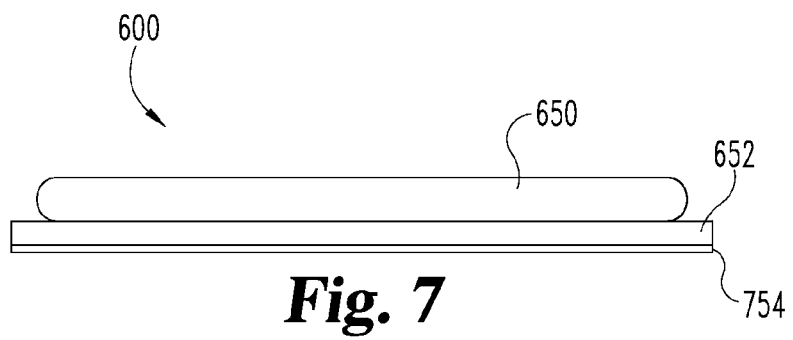
FIG. 7 is an elevational side view of one embodiment of the wire-retaining member shown in FIG. 6.

FIGS. 6 and 7 illustrate a wire-retaining assembly 600 having a wire-retaining member 650 coupled to a base 652 and an adhesive 754. In some embodiments, the base 652 is positioned between the wire-retaining member 650 and the adhesive 754, effectively coupling the wire-retaining member 650 to the adhesive 754. This arrangement allows for one to secure the wire-retaining member 650 to a surface, such as the skin of a patient, by use of the adhesive 754.

In some embodiments, the base 652 adds support for the wire-retaining member 650. For example, the base 652 may keep the wire-retaining member from bending out of plane and/or forming a kink. A sharp bend and/or kink in the wire-retaining member 650 and the inner lumen containing a proximal portion of a marker wire may limit the slidable relationship between the proximal portion of the marker wire and the wire-retaining member 650 and ultimately result in movement of the distal portion of the marker wire with respect to the lesion and/or discomfort to the patient.

Figure 8:
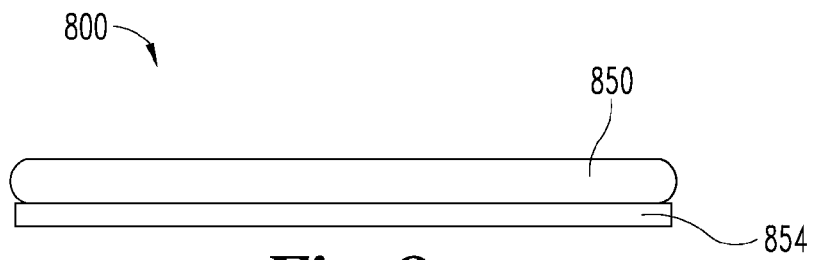
FIG. 8 is an elevational side view of one embodiment of a wire-retaining member.

As illustrated in FIG. 8, the wire-retaining assembly 800 may simply comprise a wire-retaining member 850 and an adhesive 854 without including a base. The adhesive 854 may be used to couple the wire-retaining member 850 to the skin of a patient. In other instances, the adhesive 854 may be used to couple the wire-retaining member 650, 850 to the clothing of a patient, such as a hospital gown.

The base 652 and/or adhesive 754, 854 may extend beyond the outer boundary of the wire-retaining member 650. (See e.g., FIGS. 6 and 7). For example, the base 652 and/or adhesive 754, 854 may extend beyond the area between the wire-retaining member 650 and the skin of the patient. In some instances, the base 652 and/or adhesive 754, 854 extend to an area within the loop formed by the wire-retaining member 650, such as the loop formed by the curved portion 405 of the wire-retaining member 400. In some embodiments the base 652 and/or adhesive 754, 854 extend between the distal portion 402 and proximal portion 404 of the wire-retaining member 600. Alternatively, the base 652 and/or adhesive 754, 854 may be limited to positions substantially underneath portions of the wire-retaining member 850, as shown in FIG. 8.

Extending the base 652 and/or adhesive 754, 854 beyond the area of the wire-retaining member 650 may provide an indicator and/or a visually appealing surface. For example, information pertaining to the patient, procedure, and/or the lesion may be displayed on the portion of the base 652 and/or adhesive 754, 854 extending beyond the retaining member 650. Displaying information, such as the size and/or location of the lesion within the breast on the base 652 and/or adhesive 754/854 may be beneficial for surgeons in the surgical theater.

In some embodiments, the wire-retaining member 650, 850, base 652 and/or adhesive 754, 854 may be colored to help in concealing the device and/or provide a pleasant visual appearance. For example, the patient may be provided with a selection of colors to choose from that will best allow the patient to conceal the wire-retaining member 650, 850 prior to removal in the surgical theater. The patient may also choose a particular color based on the personal preference of that individual patient. The wire-retaining member 650, 850, base 652 and/or adhesive 754, 854 may be any of a variety of colors. For instance, the wire-retaining member 650, 850 may be pink to symbolize breast cancer awareness.

In some instances, a protective cover may be removably positioned over the adhesive 754, 854 to protect the adhesive during manufacture, shipping, and/or storage. Prior to attaching the wire-retaining member to the body of a patient, a medical professional may remove the protective cover so as to expose the adhesive.

In some embodiments, adhesive 754, 854 and/or base member 652 may define an opening for receiving a marker wire. For example, a portion of adhesive 754, 854 and/or base member 652 positioned between the wire-retaining member 650, 850 and the skin of the patient may defined a opening that communicates with an aperture defined by the side wall of the wire-retaining member 650, 850. Advantageously, this type of arrangement may allow for protection of the marker wire between the point at which it exits the skin of the patient and enters the wire-retaining member 650, 850.

Figure 9:
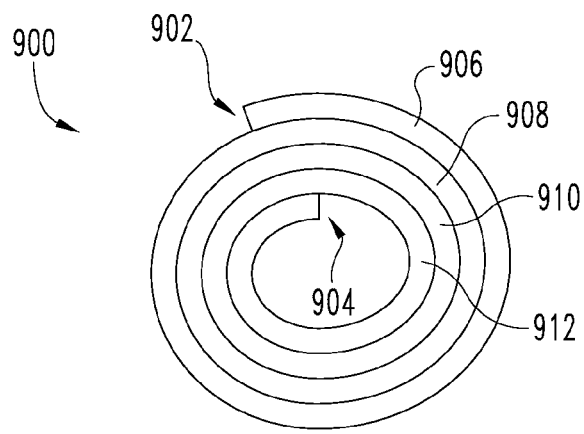
FIG. 9 is a plan view of one embodiment of a wire-retaining member.

FIG. 9 illustrates an embodiment of a wire-retaining member 900 that extends in an inward spiral direction from a distal portion 902 to a proximal portion 904, passing through loops 906, 908, 910 and 912. This type of arrangement may allow for a more compact wire-retaining member 900 that has both a low profile and occupies a reduced surface area on the skin or clothing of a patient. This type of arrangement may also accommodate a greater length of proximal portion of a marker wire and therefore may be useful for applications in which the lesion is close to the surface of the skin and more of the marker wire is positioned outside of the body than for similar marker wires marking the location of a lesion deeper within the breast.

The arrangement shown in FIG. 9 may also be used to reduce the contact of foreign objects such as skin and clothing with the portion of the marker wire extending from inside of the body of the patient and/or with the penetration/access site. For example, the proximal portion of the marker wire may be inserted first into the proximal portion 904 of the wire-retaining member to orient the wire-retaining member 900 into position around the location where the marker wire enters the body of the patient (i.e., the access site). With the access site positioned near the proximal portion 904 of the wire-retaining member 900, the loops 906, 908, 910, and 912 may surround the access site and/or the exposed portion of the marker wire, protecting the access site and/or the marker wire from contact with foreign objects. Orienting the wire-retaining member 900 in this manner may also aid in marking the access site for medical personal and/or the patient by forming a type of bulls-eye arrangement around the access site. Similarly, the wire-retaining member 900 may be used to mark a desired location for incision for later biopsy and/or removal of the lesion from the body.

Figure 10:
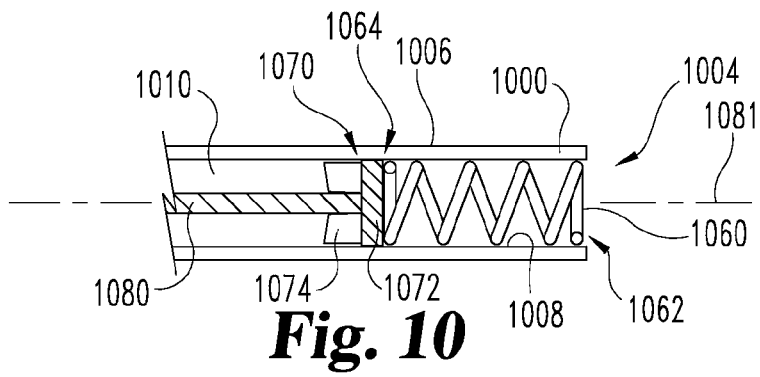
FIG. 10 is a cross-sectional view of one embodiment of a wire-retaining member having a movement-resisting member.

FIG. 10 illustrates an embodiment of a wire-retaining member 1000 having a movement-resisting member. The wire-retaining member 1000 has a proximal portion 1004 which has an outer surface 1006 and an inner surface 1008 that defines an inner lumen 1010. A spring member 1060 is positioned within the inner lumen 1010 in the proximal portion 1004 of the wire-retaining member 1000. A proximal portion 1062 of the spring member 1060 is coupled to the inner surface 1008 of the proximal portion 1004 that defines the inner lumen 1010. A distal portion 1064 of the spring member 1060 is coupled to a coupling member 1070 that coupled the spring member 1060 to a marker wire 1080. In some instances, the coupling member has a spring coupling portion 1072 and a wire coupling portion. The spring coupling portion 1072 can be arranged to couple to the distal portion 1064 of the spring member 1060, and the wire coupling portion 1074 can be arranged to couple to the marker wire 1080 that marks a site within a patient. The spring member 1060, coupling member 1070, and wire coupling portion 1074 cooperate together as a movement-resisting member that resists the movement of the marker wire 1080 with respect to the wire-retaining member 1000.

For example, as the marker wire 1080 is advanced towards the proximal portion 1004 of the wire-retaining member 1000, the spring member 1060 of the movement-resisting member compresses and the movement-resisting member exerts a movement-resisting force (in a distal direction) against the proximal movement of the marker wire 1080. Similarly, as the marker wire 1080 is advanced in a distal direction, the spring member 1060 expands and the movement-resisting member exerts a movement-resisting force (in a proximal direction) on the marker wire 1080 that resists the distal movement of the marker wire 1080. Therefore, this sort of arrangement may be used to resist movement of the marker wire 1080 in one or more directions along a longitudinal axis 1081 of the marker wire 1080. This arrangement may also be used to return the marker wire 1080 to a desired orientation with respect to the wire-retaining member 1000.

An arrangement such as the movement-resisting member shown in FIG. 10 may also be used to apply a predetermined force in response to movement of the marker wire 1080. For example, the spring member 1060 may be arranged to have a predetermined, linear spring constant such that the force applied to the marker wire 1080 by the movement-resisting member varies (e.g., increases) as the relative movement between the marker wire 1080 and the wire-retaining member 1000 varies (e.g., increases).

Other arrangements of a movement-resisting member are contemplated. For example, the arrangement shown in FIG. 10 may be modified by removing the spring member 1060 from the movement-resisting member. This would leave the wire coupling portion 1074 and/or the coupling member 1070 coupled to the proximal portion of the marker wire 1080. The wire coupling portion 1074 and/or the coupling member 1070 may resist movement of the proximal portion of the marker wire 1080 in a direction towards the inner surface 1008 of the wire-retaining member 1000. In some embodiments, the spring coupling portion 1072 and/or the wire coupling portion 1074 may substantially fill a cross-sectional area of the inner lumen 1010 and thus serve as a mechanical damper, such as a dashpot and/or plunger. This damper and/or plunger arrangement may resist movement in one or more directions along the longitudinal axis 1081 of the marker wire 1080 without applying a force upon the marker wire 1080 to return it to an initial position, such as a spring member 1060 may.

Figure 11:
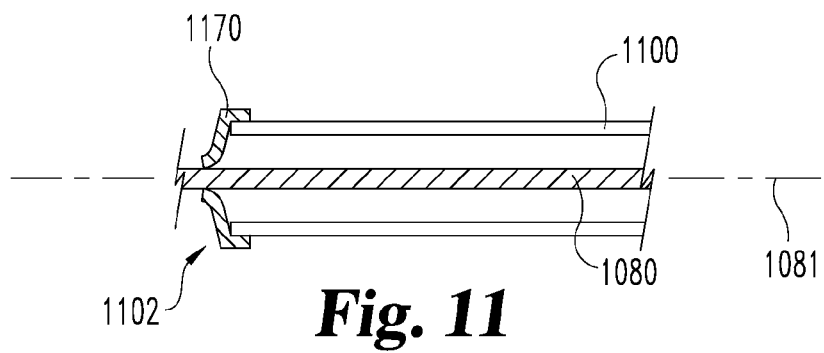
FIG. 11 is a cross-sectional view of one embodiment of a wire-retaining member having a movement-resisting member.
Figure 12:
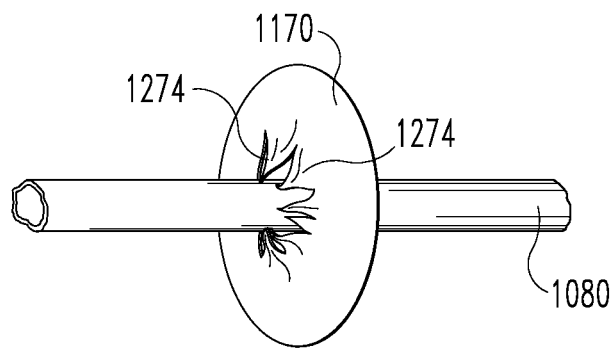
FIG. 12 is a perspective view of one embodiment of a movement-resisting member.

FIGS. 11 and 12 illustrate other embodiments of a movement-resisting member. The wire-retaining member 1100 has a distal region 1102 with a resisting member 1170 that resists the movement of a marker wire 1080. The resisting member 1170 may resist the movement of the marker wire 1080 in multiple directions or in a single direction. For example, the movement-resisting member 1170 may resist movement of the marker wire 1080 towards a wall of the wire-retaining member 1100 in the distal region 1102; and/or movement of the marker wire 1080 in a direction along the longitudinal axis 1081 of the marker wire 1080, such as in a proximal direction, a distal direction, or both.

In some instances, the resisting member 1170 may comprise tab portions 1274 that contact the surface of the marker wire 1080 and frictionally resist movement in one or multiple longitudinal directions. In some instances, tab portions 1274 are deflectable. A deflectable tab portion 1274 may be used to provide resistance to movement of the marker wire in a longitudinal direction, such as in a proximal direction (into the inner lumen of the wire-retaining member 1100) or a distal direction (outward of the wire-retaining member 1100) or both. In some embodiments, tab portions 1274 may resemble the flaps found on lids for cups, such as the flaps allowing a straw to access the cavity formed by the cup.

In some embodiments, the resisting member 1170 may resist movement in multiple directions. These embodiments, the resisting member 1170 may provide equal resistance to movement in multiple directions or may provide greater resistance to movement in some directions than others. For example, the movement-resisting member 1170 may be arranged to provide a greater resistance to movement in a first direction than the movement-resisting member 1170 provides in a second direction.

A movement-resisting arrangement, such as that shown in FIG. 11, that continually resists movement along the length of the proximal portion of the marker wire 1080 and/or applies a constant resistive force may be preferred in some instances. For example, a physician may not wish to have a variable force applied to the marker wire, such as that capable with the embodiment illustrated in FIG. 10. A physician may simply wish to resist the withdrawal of the marker wire 1080 from the inner lumen of the wire-retaining member 1100 so as to maintain much of the marker wire 1080 within the inner lumen and the wire-retaining member 1100 and/or to apply a slight tension against the distal portion of the marker wire 1080 positioned at/near a lesion within the body of the patient. Advantageously, applying slight tension to the distal portion that is anchored within the patient may reduce the likelihood of marker wire migration.

Figure 13:
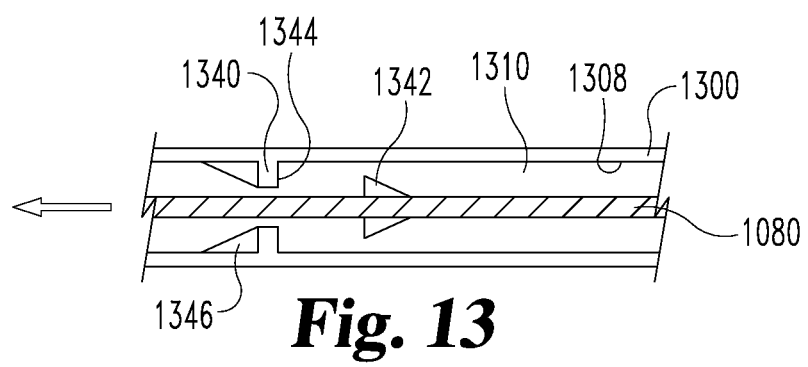
FIG. 13 is a cross-sectional view of one embodiment of a wire-retaining member having a movement-resisting member.

FIG. 13 illustrates an embodiment of a movement-resisting member that limits the distance a marker wire 1080 may move within a wire-retaining member 1300. In this embodiment, the wire-retaining member 1300 has a flange member 1340 extending off an inner surface 1308 into the inner lumen 1310. The flange member 1340 is arranged to contact a stop member 1342 positioned on and/or coupled to the marker wire 1080 when the marker wire is moved along a longitudinal direction.

As shown in FIG. 13, when the marker wire 1080 is moved in the direction indicated by the arrow, the stop member 1342 contacts the surface 1344 of the flange member 1340 so as to stop the marker wire 1080 from being completely withdrawn from the inner lumen 1310 of the wire-retaining member 1300. In some instances, the stop member 1342 can have a side that slants towards the marker wire 1080. Advantageously, this may permit the stop member 1342 to be advanceable past a flange member 1340 in one direction and/or resist movement of the marker wire 1080 and stop member 1342 in another direction. In some instances, this movement-resisting arrangement may be preferred since it may limit the distance that a marker wire 1080 may move in one or more directions along the inner lumen 1310 of the wire-retaining member 1300.

For example, in some embodiments, the wire-retaining member 1300 may have a ramp portion 1346 leading up to the flange member 1340 so that when the marker wire 1080 is first being advanced through the wire-retaining member 1300 in a direction opposite the arrow, the stop member 1342 contacts the ramp portion 1346, potentially centering the marker wire 1080 in the inner lumen 1310. In some embodiments, the arrangement of the ramp portion 1346 and the stop member 1342 allow for the stop member 1342 to advance past the flange member 1340 to be on the opposite side of the flange member 1340 than the ramp portion 1346. For example, stop member 1342, ramp portion 1346, and/or flange member 1340 may be arranged so that as marker wire 1080 is advanced into the wire-retaining member 1300, stop member 1342 contacts ramp portions 1346 and ramp portions 1346 separate so as to allow stop member 1342 to advance past the ramp portions 1346 and flange member 1340 to reach the proximal side of surface 1344.

Figure 14:
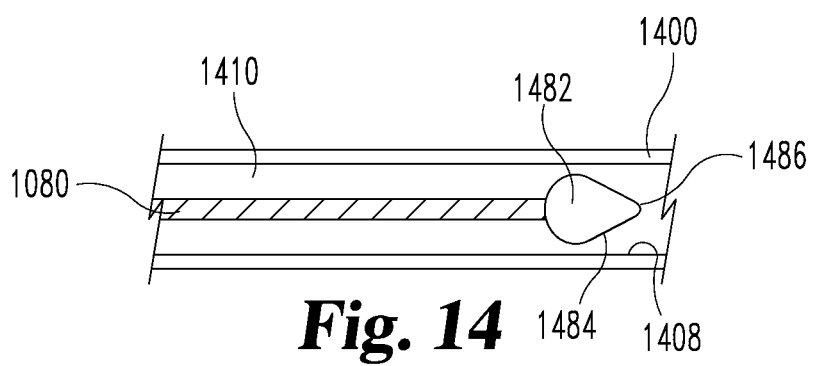
FIG. 14 is a cross-sectional view of one embodiment of a wire-retaining member and the proximal end of a marker wire.

FIG. 14 illustrates a wire-retaining member 1400 having an inner surface 1408 defining an inner lumen 1410. The inner lumen 1410 is arranged to receive a marker wire 1080 having a guiding member 1482 positioned on a proximal portion of the marker wire 1080. The guiding member 1482 may aid in sliding movement of the marker wire 1080 within the inner lumen 1410 by preventing the tip of the marker wire 1080 from catching on the inner surface 1408 of the wire-retaining member 1400 and/or by preventing the marker wire 1080 from coiling within the inner lumen 1410.

In some embodiments, the guiding member 1482 may have slanted portions 1484. The slanted portions 1484 may aid in guiding the movement of the proximal portion of the marker wire 1080 through the inner lumen 1410 of the wire-retaining member 1400. The slanted portions 1484 may also be arranged to center the guiding member 1482 within the inner lumen 1410. In some instances, centering the guiding member 1482 within the inner lumen 1410 may also center the proximal portion of the marker wire 1080 within the inner lumen 1410 of the wire-retaining member 1400, reducing friction between the proximal portion of the marker wire 1080 and the inner surface 1408. The slanted portion 1484 may also aid in the insertion of the marker wire 1080 into a distal and/or proximal opening of the wire-retaining member 1400.

The slanted portions 1484 may be angled in a proximal direction towards a guiding member tip 1486. The guiding member tip 1486 at the end of the slanted portion 1484 may be curved so as to prevent catching or binding on the inner surface 1408 of the wire-retaining member 1400.

Figure 15:
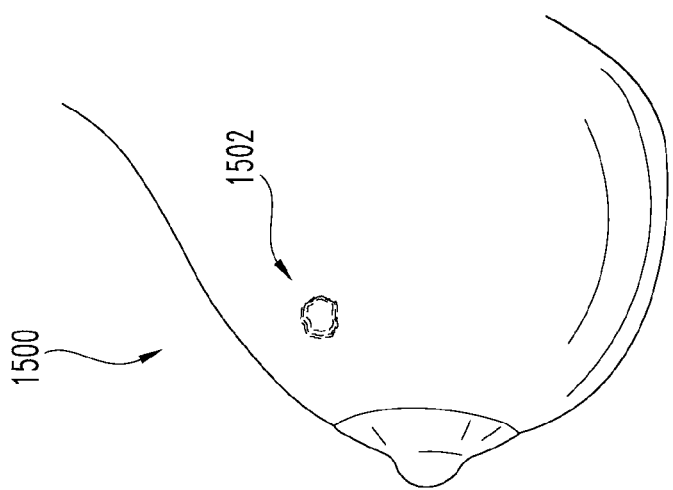
FIGS. 15, 16, 17, and 18 illustrate a method of inserting a marker wire to mark the location of a lesion within the breast and the retention of the marker wire in a wire-retaining member.
Figure 16:
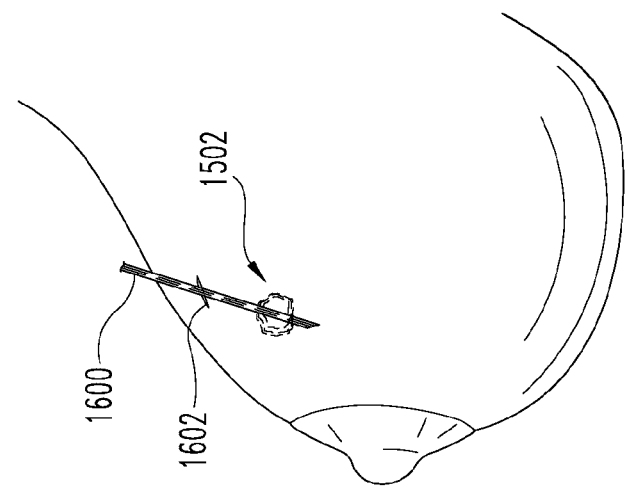
Figure 17:
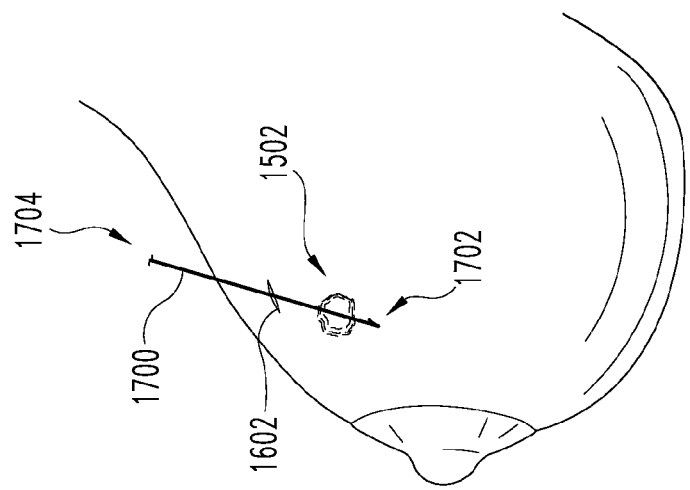
Figure 18:
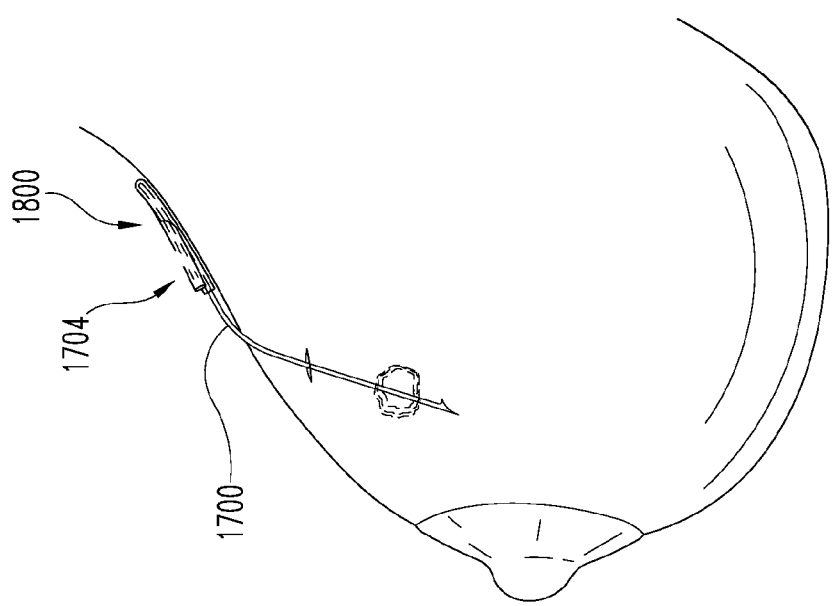

FIGS. 15, 16, 17, and 18 illustrate a method of inserting a breast lesion localization marker wire and using a wire-retaining member to secure the breast lesion localization marker wire against the skin of a patient. FIG. 15 illustrates a breast 1500 of a patient having a lesion 1502 located beneath the surface of the skin. FIG. 16 illustrates a breast lesion localization needle 1600 advanced to a lesion 1502 through an access site 1602 in the skin of a patient. FIG. 17 illustrates a marker wire 1700 after it has been advanced through the breast lesion localization needle 1600 and the breast lesion localization needle 1600 has been withdrawn from the lesion 1502 through the tissue of the breast 1500 and out of the access site 1602, so as to leave a distal portion 1702 of the marker wire 1700 residing within the breast 1500 near the lesion 1502, and a proximal portion 1704 of the marker wire 1700 residing outside of the breast 1500. FIG. 18 illustrates a wire-retaining member 1800 positioned over the proximal portion 1704 of the marker wire 1700 and secured to the skin of the patient.

Figure 19:
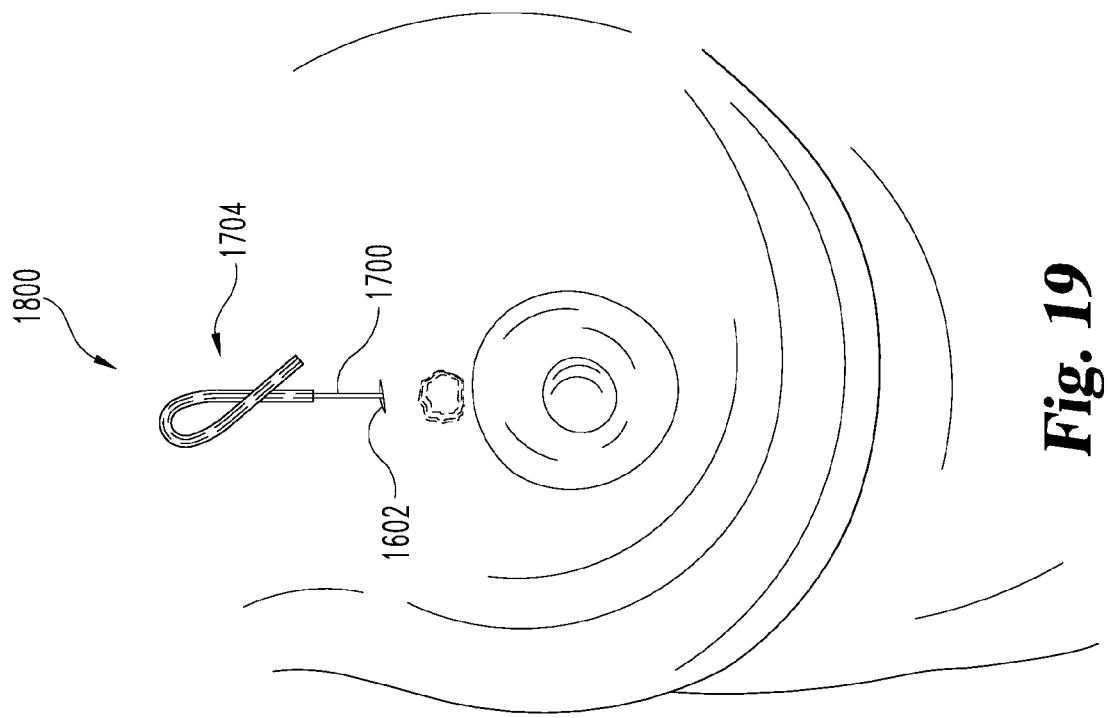
FIG. 19 illustrates a wire-retaining member and a marker wire that marks a lesion inside of a breast.

FIG. 19 illustrates a front elevational view of the breast 1500 of a patient having a wire-retaining member 1800 positioned on the surface of the skin and retaining a proximal portion 1704 of a marker wire 1700 that advances through an access site 1602 in the patient's skin towards a lesion 1502 beneath the surface of the skin of a patient's breast 1500. A portion of the wire marker 1700 may be exposed between the access site 1602 and the wire-retaining member 1800 and/or the wire-retaining member 1800 may retain the marker wire 1700 substantially up to the location of the access site 1602.

Figure 20:
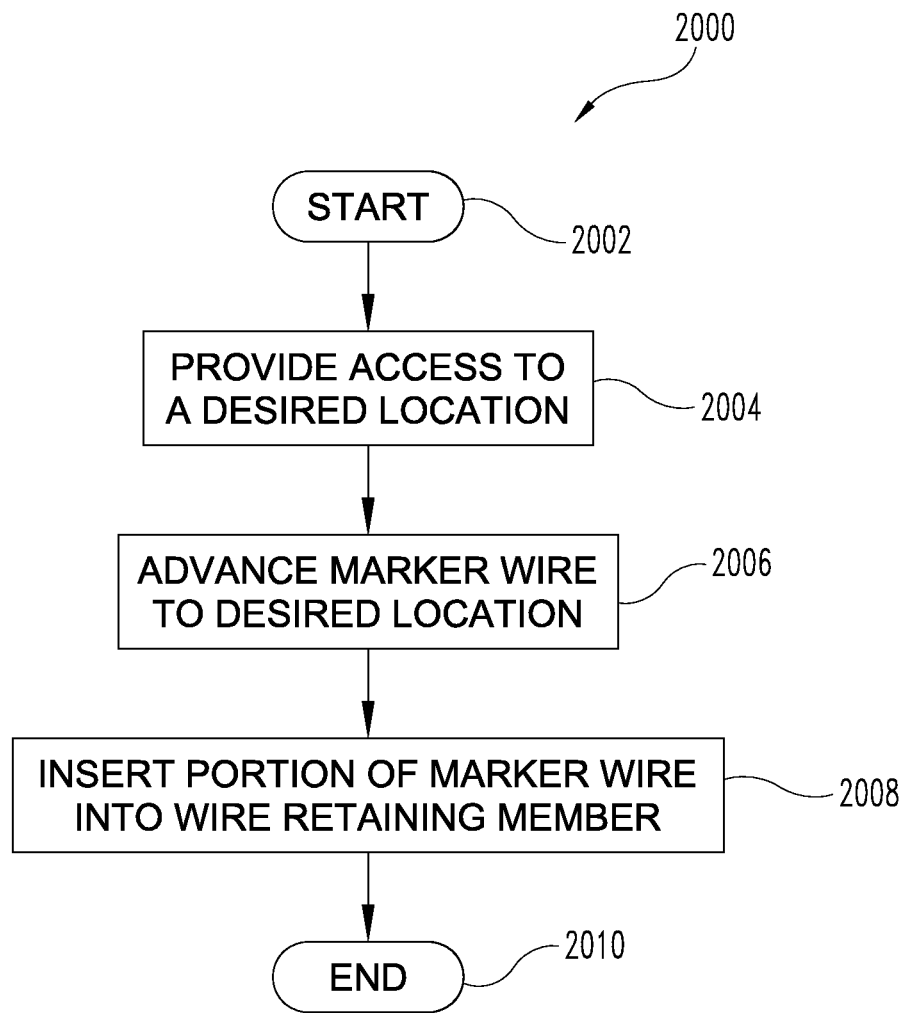
FIG. 20 is a flow chart illustrating a method of inserting and securing a marker wire.

FIG. 20 illustrates a flow chart 2000. The flow chart illustrates a method of positioning a marker wire near a lesion in a breast of a patient and securing a proximal portion of that marker wire to the skin of a patient. In stage 2002 a marker wire and wire-retaining member are obtained or otherwise provided in any number of manners. For instance, the marker wire and/or retaining member may be purchased from a medical device vendor. In stage 2004, a breast lesion localization needle may be used to provide access to a desired location within the breast near the location of a lesion. In stage 2006, a breast lesion localization marker wire may be advanced through a lumen within the breast lesion localization needle towards the lesion site. The breast lesion localization needle may be withdrawn over the marker wire to leave a distal portion of the marker wire near the lesion and completely remove the breast lesion localization needle from the tissue of the patient and the marker wire. In stage 2008, a proximal portion of the breast lesion localization marker wire may be inserted into a wire-retaining member and the wire-retaining member may be positioned adjacent to the patient's skin. The wire-retaining member may be attached to the skin of a patient, such as by use of an adhesive. In stage 2010, the access site may be treated to prevent excess bleeding.

Figure 21:
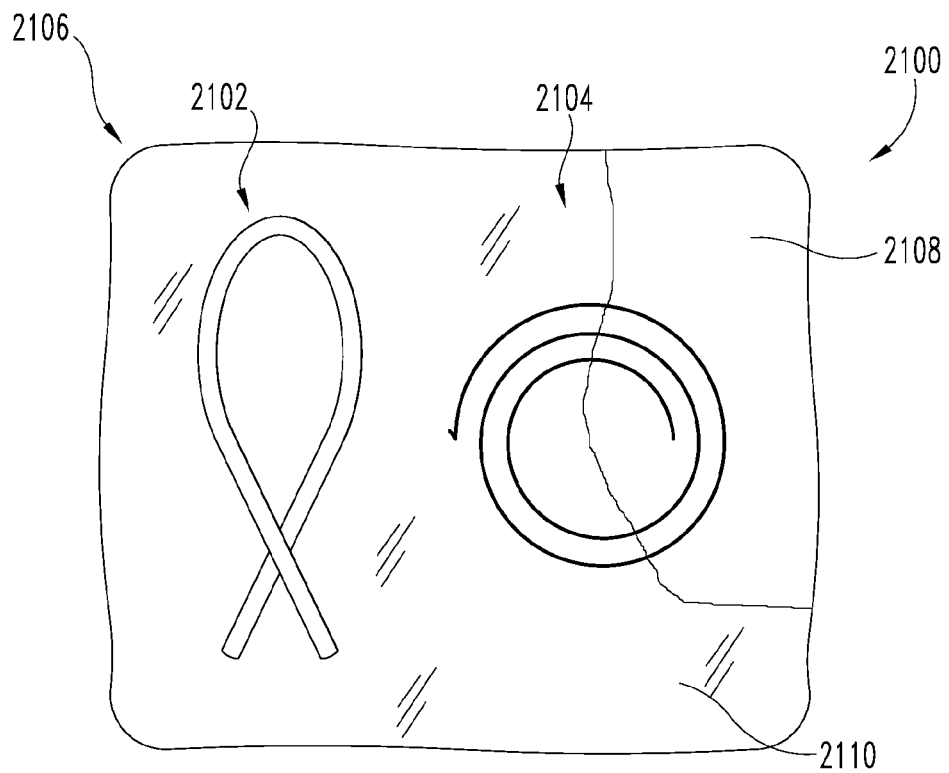
FIG. 21 is a plan view of a kit containing a wire-retaining member and a marker wire.

FIG. 21 illustrates a kit 2100 comprising a wire-retaining member 2102 and a corresponding breast lesion localization marker wire 2104. Preferably, the wire-retaining member 2102 and the breast lesion localization marker wire 2104 can be individually and/or jointly contained within a sealed and sterile package, such as packaging member 2106. For example, the wire-retaining member 2102 and/or the breast lesion localization marker wire 2104 can be packaged within a packaging including a backing layer and a front film layer that are joined by a boundary of pressure-adhesive as is conventional in medical packaging, wherein the contents of the packaging are sealed between the backing layer and front film layer. Sterilization of such a medical product may be achieved, for example, by irradiation, ethylene oxide gas, or any other suitable sterilization technique, and the materials and other properties of the medical packaging will be selected accordingly.

In some instances, the packaging member 2106 may be comprised of separate packaging portions such as a first sheet 2108 and a second sheet 2110, and the packaging member 2106 may confine the wire-retaining member 2102 and the breast lesion localization marker wire 2104 between the first and second sheets 2108, 2110. For example, the first sheet 2108 and second sheet 2110 may sandwich the wire-retaining member 2102 and the marker wire 2104 between the first sheet 2108 and the second sheet 2110. In some instances, the first sheet 2108 and second sheet 2110 are sealed around the wire-retaining member 2102 and the breast lesion localization marker wire 2104 so as to form a hermetically sealed container.

Figure 22:
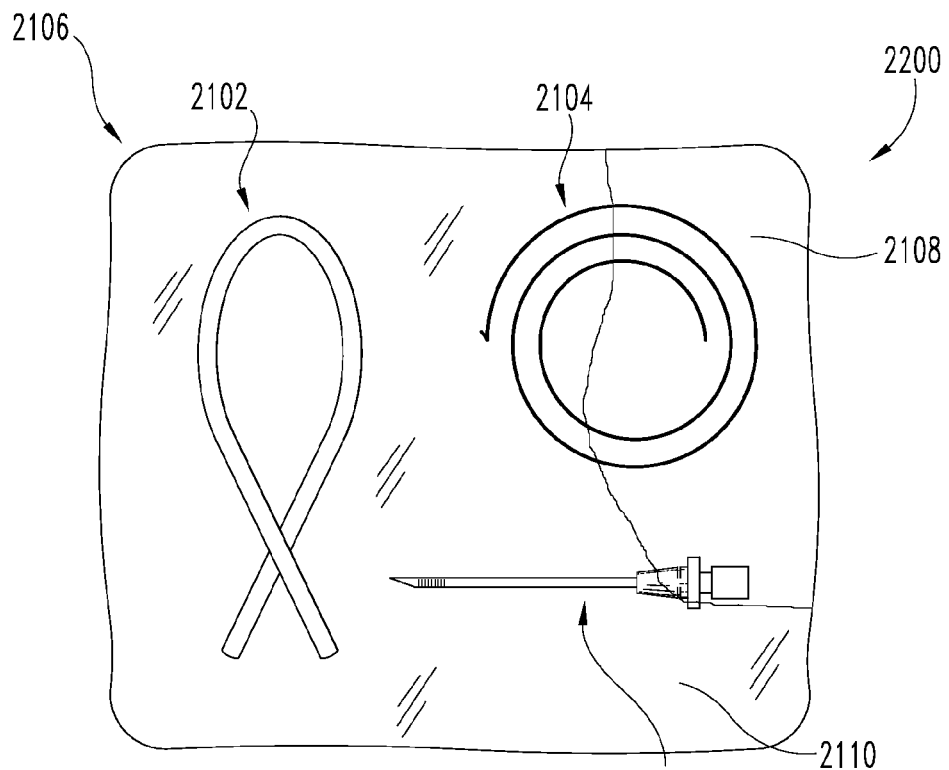
FIG. 22 is a plan view of a kit containing a wire-retaining member, a marker wire, and a localization needle.

As will be appreciated by one of ordinary skill in the art, a kit comprising a wire-retaining member may also include other components useful in the placement and/or securing of a lesion localization marker wire. For example, FIG. 22 illustrates a kit 2200 comprising a wire-retaining member 2102, a breast lesion localization marker wire 2104, a breast lesion localization needle 2212, and a packaging member 2106. Similar to the discussion above, the packaging member 2106 may confine the wire-retaining member 2102, the breast lesion localization marker wire 2104, and the breast lesion localization needle 2212 in the same compartment or in separate compartments, and, in some instances, may sandwich the wire-retaining member 2102, the breast lesion localization marker wire 2104, and the breast lesion localization needle 2212 between a first sheet 2108 a second sheet 2110. As will be appreciated by those of ordinary skill in the art, the packaging member may be sealed in any number of ways such as by heat bonding or adhering the first and second sheets 2108, 2110 of the packaging member 2106 together around the wire-retaining member 2102, the breast lesion localization marker wire 2104, and the breast lesion localization needle 2212 and/or between two or more or all of them.

It should be recognized by one of ordinary skill in the art that any alterations, further modifications and/or any further applications of the principles of the invention as described herein, as would normally occur to one skilled in the art, are contemplated.

While the invention has been illustrated and described in detail in the drawings and foregoing description, the same is to be considered as illustrative and not resistive in character, it being understood that the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

What is claimed is:

1. A kit, comprising:
   a packaging member retaining:
   a marker wire having a distal end region arranged for securement in a desired location inside a patient and a proximal end region having a proximal wire portion; and
   a wire-retaining member arranged to be secured to the patient and receive said proximal wire portion;
   wherein said wire-retaining member slidably couples said proximal wire portion of said marker wire to the patient; and wherein the marker wire has withdrawal-resisting member at the distal end region.

2. The kit of claim 1, wherein:
   said wire-retaining member confines movement of said marker wire to a direction substantially along the length of said proximal wire portion.

3. The kit of claim 1, further comprising:
   an adhesive member on said wire-retaining member arranged to couple said wire-retaining member to the body of a patient.

4. The kit of claim 3, wherein the adhesive member is located between the wire-retaining member and the patient when the wire-retaining member is secured to the patient.

5. The kit of claim 1, wherein:
   said wire-retaining member comprises a tube defining an internal lumen arranged to receive said proximal wire portion.

6. The kit of claim 5, wherein:
   said tube comprises a curved portion and a first opening communicating with said internal lumen and arranged to receive said marker wire.

7. The kit of claim 1, wherein a length of the wire-retaining member defines a loop.

8. A marker wire retaining device, comprising:
   a wire-retaining member arranged to be secured to a patient and defining a wire receiving region arranged to receive a proximal wire portion of a marker wire; and
   an adhesive member arranged to couple said wire-retaining member to the patient, the adhesive member being located between the wire-retaining member and the patient when the wire-retaining member is secured to the patient and a marker wire having a withdrawal-resisting member at a distal end region arranged for securement in a desired location inside a patient and a proximal end region having a proximal wire portion;
   wherein said wire-retaining member slidably couples said proximal wire portion to the patient.

9. The marker wire retaining device of claim 8, wherein:
   said wire receiving region defines a path having a curved portion.

10. The method of claim 9, wherein said wire-retaining member comprises a ribbon shape.

11. The method of claim 9, wherein said wire-retaining member comprises a coil shape.

12. The marker wire retaining device of claim 8, wherein a length of the wire-retaining member defines a loop.

13. A method, comprising:
    advancing a marker wire through a penetration site in skin of a patient to a desired location within the patient such that a distal end region of the marker wire secures in the desired location and said marker wire extends from the desired location proximally through the skin of the patient to a proximal end region having a proximal wire portion;
    inserting said proximal wire portion of said marker wire into a wire-retaining member;
    advancing said wire-retaining member towards the penetration site and not advancing said wire-retaining member through said penetration site; and
    securing said wire-retaining member to the skin of the patient; wherein the distal end region of the marker wire is a arranged for securement in the desired location inside the patient; wherein the wire-retaining member is arranged to be secured to the patient and receive said proximal wire portion to slidably couple said proximal wire portion of said marker wire to the patient; and wherein the marker wire has a withdrawal-resisting member at the distal end region.

14. The method of claim 13, wherein securing said wire-retaining member includes adhesively securing said wire-retaining member.

15. A marker wire retaining device, comprising:
    a wire-retaining member including an elongate tube having a distal portion, a proximal portion, and a curved portion positioned between said distal portion and said proximal portion;
    said elongate tube defining an inner lumen that extends from said distal portion, through said curved portion, and into said proximal portion;
    wherein said distal portion and said proximal portion cross one another in a coincident region; and
    wherein said distal portion defines a groove arranged to receive said proximal portion in said coincident region so as to decrease the height profile of the device in the coincident region.

16. The marker wire retaining device of claim 15, wherein said inner lumen of said first portion communicates with said inner lumen of said second portion in said coincident region.

\* \* \* \* \*